United States Patent
Khristov et al.

(10) Patent No.: US 11,819,020 B2
(45) Date of Patent: Nov. 21, 2023

(54) DEVICES FOR TISSUE CRYOPRESERVATION AND RECOVERY

(71) Applicant: The United States of America, as represented by the Secretary, Department of Health and Human Services, Bethesda, MD (US)

(72) Inventors: Vladimir Rouskov Khristov, Washington, DC (US); Arvydas Miminishkis, Bethesda, MD (US); Kapil Bharti, Potomac, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 281 days.

(21) Appl. No.: 16/478,093

(22) PCT Filed: Jan. 31, 2018

(86) PCT No.: PCT/US2018/016101
§ 371 (c)(1),
(2) Date: Jul. 15, 2019

(87) PCT Pub. No.: WO2018/144515
PCT Pub. Date: Aug. 9, 2018

(65) Prior Publication Data
US 2019/0343113 A1 Nov. 14, 2019

Related U.S. Application Data

(60) Provisional application No. 62/453,148, filed on Feb. 1, 2017.

(51) Int. Cl.
*A01N 1/02* (2006.01)

(52) U.S. Cl.
CPC .......... *A01N 1/0242* (2013.01); *A01N 1/0252* (2013.01)

(58) Field of Classification Search
CPC ... A01N 1/0242; A01N 1/0252; A01N 1/0263
See application file for complete search history.

(56) References Cited

U.S. PATENT DOCUMENTS 5,964,096 A * 10/1999 Watson .................... A01N 1/02
                                                        435/297.5
8,388,912 B2   3/2013 Schryver
(Continued)

FOREIGN PATENT DOCUMENTS

JP    11-512924 A    11/1999
JP    2001-514866 A   9/2001
(Continued)

OTHER PUBLICATIONS

Liu et al., ROCK Inhibitor and Feeder Cells Induce the Conditional Reprogramming of Epithelial Cells, Feb. 2012, The American Journal of Pathology, vol. 180, Issue 2, pp. 599-607 (Year: 2012).*
(Continued)

*Primary Examiner* — Michael L Hobbs
*Assistant Examiner* — Lenora A Abel
(74) *Attorney, Agent, or Firm* — Leydig, Voit & Mayer, Ltd.

(57) ABSTRACT

Disclosed devices for recovering cryopreserved tissue can comprise a receptacle that receives a sealed, frozen tissue container containing cryopreserved tissue and cryopreservation media, with at least one recovery media chamber and a waste material chamber fluidly coupled to the tissue container receptacle. The recovery device can be inserted into a regulator apparatus that facilitates thawing and warming of the media and tissue, and regulation of the flow of recovery media through the tissue container to flush out the (Continued)

thawed cryopreservation media into the waste chamber. The regulator can identify the tissue based on an ID tag on the tissue container and automatically apply an appropriate algorithm for thawing, culturing, and maintaining the tissue in a viable state.

19 Claims, 13 Drawing Sheets

(56) References Cited

U.S. PATENT DOCUMENTS

| | | | |
|---|---|---|---|
| 8,647,311 B2 | 2/2014 | Dib | |
| 9,297,499 B2 | 3/2016 | Jimenez-Rios et al. | |
| 2006/0131196 A1* | 6/2006 | Fuhr | A01N 1/02 206/438 |
| 2007/0257039 A1* | 11/2007 | Chammas | A01N 1/0263 220/500 |
| 2011/0277486 A1 | 11/2011 | Zimmermann et al. | |
| 2013/0115691 A1 | 5/2013 | Schryver | |
| 2014/0083212 A1 | 3/2014 | Schryver et al. | |
| 2015/0087052 A1* | 3/2015 | Cullis | A01N 1/0268 435/307.1 |
| 2015/0125954 A1* | 5/2015 | Zimmermann | C12M 45/22 435/366 |
| 2015/0140656 A1 | 5/2015 | Hernan Izquierdo et al. | |
| 2016/0021873 A1 | 1/2016 | Akuta et al. | |

FOREIGN PATENT DOCUMENTS

| | | | |
|---|---|---|---|
| JP | 2016-533197 A | 10/2016 | |
| WO | WO 96/24018 | 8/1996 | |
| WO | WO 97/00943 A1 | 1/1997 | |
| WO | WO 99/08513 A1 | 2/1999 | |
| WO | WO 2007/028243 | 3/2007 | |
| WO | WO 2011/146998 | 12/2011 | |
| WO | WO-2011146998 A1 * | 12/2011 | ........... A01N 1/0268 |
| WO | WO 2012/158963 | 11/2012 | |
| WO | WO 2013/187077 A1 | 12/2013 | |
| WO | WO 2015/035071 | 3/2015 | |
| WO | WO 2015/048003 A1 | 4/2015 | |
| WO | WO 2015/175819 | 11/2015 | |
| WO | WO-2015175819 A1 * | 11/2015 | .............. A47J 36/32 |
| WO | WO 2016/167332 | 10/2016 | |

OTHER PUBLICATIONS

Wright, et al., Enhanced viability of corneal epithelial cells for efficient transport/storage using a structurally-modified calcium alginate hydrogel, 2012, Regenerative Medicine, 7 (3). pp. 295-307. (Year: 2012).*

International Search Report and Written Opinion for related International Application No. PCT/US2018/016101, dated May 16, 2018, 17 pages.

Malpique et al., "Alginate Encapsulation as a Novel Strategy for the Cryopreservation of Neurospheres," *Tissue Engineering*, Part C, 16(5):965-973 (Oct. 1, 2010).

* cited by examiner

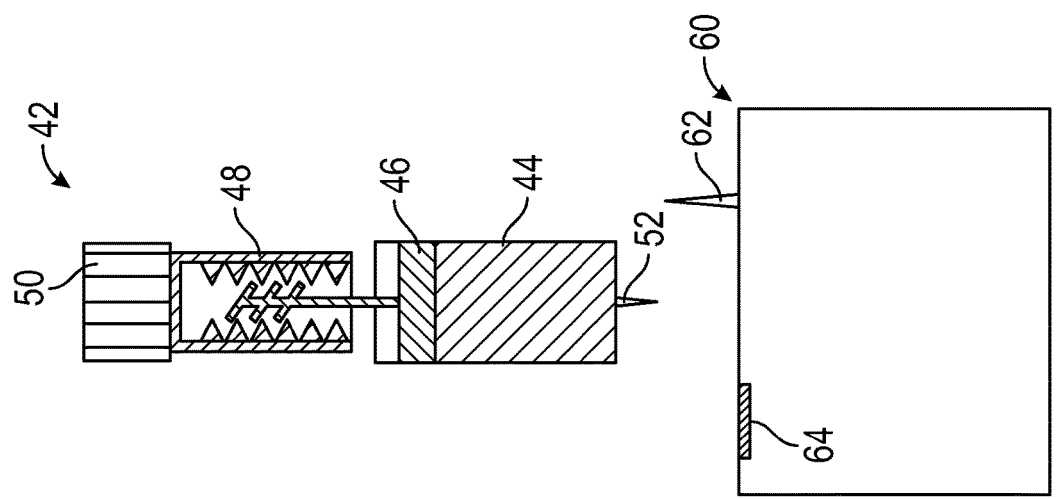
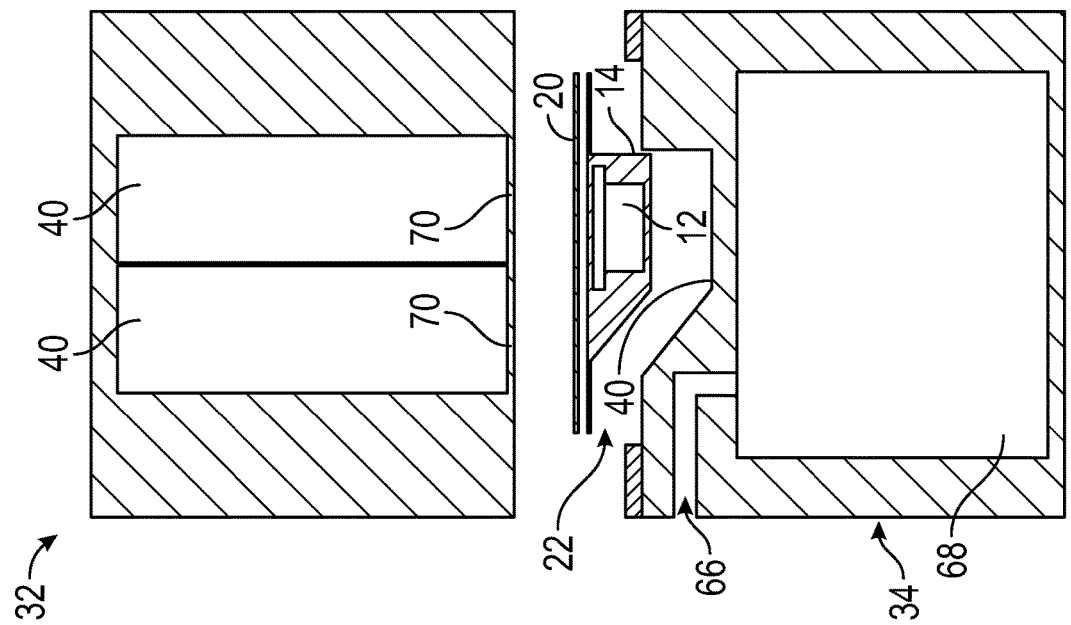
FIG. 7
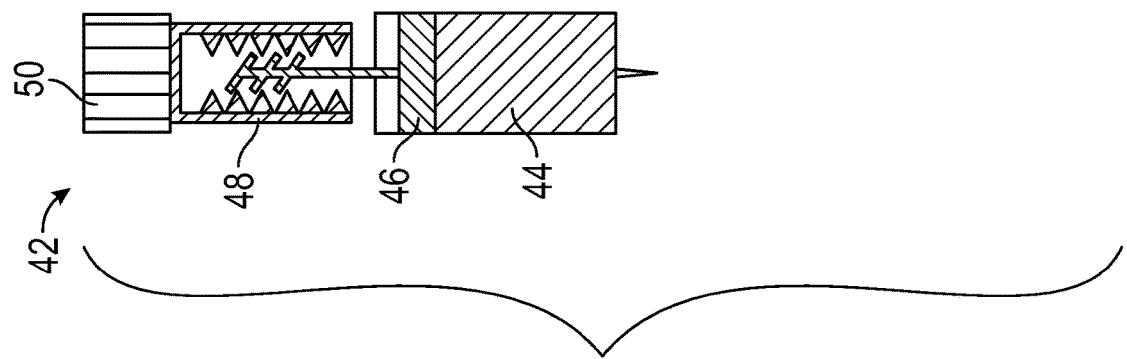

DEVICES FOR TISSUE CRYOPRESERVATION AND RECOVERY

CROSS-REFERENCE TO RELATED APPLICATIONS

This application is the U.S. National Stage of International Application No. PCT/US2018/016101, filed Jan. 31, 2018, and claims the benefit of U.S. Provisional Application No. 62/453,148, filed Feb. 1, 2017, which is herein incorporated by reference in its entirety.

STATEMENT OF GOVERNMENT SUPPORT

This invention was made with Government support under project numbers Z01#: EY00419, EY000542, EY000456, and EY000531 by the National Institutes of Health, National Eye Institute. The Government has certain rights in the invention.

FIELD

The invention relates to the field of tissue cryopreservation and recovery.

BACKGROUND

Cryopreservation is a process where living biological materials (e.g., cells, tissues) susceptible to damage caused by unregulated chemical kinetics are preserved by cooling to very low temperatures in the presence of specific cryopreservation media that protects the biological material from damage. At low enough temperatures, physical or chemical activity which might cause damage to the biological material is effectively stopped. The biological material is then thawed in a controlled manner that minimizes damage and desirably brings the material back to a viable state.

While single-cell suspensions are commonly cryopreserved, it is much more difficult to cryopreserve sheets or layers of tissues, an even more so for three-dimensional tissue constructs, such that they can be later recovered and be viable for transplantation into a patient. Layers of tissue and three-dimensional tissue constructs can suffer damage from tensional stresses experienced during expansion and contractions that occurs during freezing and thawing, for example. Uneven physical changes within the tissue during cooling or warming can also cause damage to the tissue. Further, conventional cryopreservation media can be toxic to the tissues in a non-frozen state and can render the tissues not suitable for later recovery and culturing. Another issue occurs when tissues are needed to be transferred into an operating room for transplantation purposes, which usually requires a cell culture room setup for recovering the tissue from a frozen state prior to transplantation procedures. This also imposes specific requirements to preserve sterility. For example, in a process using retinal epithelial tissue layers, the cryopreserved epithelial tissue must be manually thawed and then transferred between multiple containers for culturing and maintenance, which introduces variability, may compromise sterility, and requires special facilities including a cell culture room with highly trained personnel to complete the various steps.

SUMMARY

The disclosed technology can make the recovery, culturing, and maintenance of cryopreserved tissues simpler, faster, and less dangerous to the tissue, reduce contamination of the tissue, and require fewer human and infrastructure resources to accomplish. Disclosed devices for recovering cryopreserved tissue can comprise a tissue container receptacle that receives a sealed, frozen tissue container containing cryopreserved tissue (e.g., a tissue sheet or complex three-dimensional tissue construct) and cryopreservation media. The recovery device can also include at least one recovery media chamber configured to contain at least one reservoir of tissue recovery media that is fluidly coupled to the tissue container receptacle, and a waste material chamber that is fluidly coupled to the tissue container receptacle.

The recovery device with the frozen tissue container loaded inside can be placed in a regulator apparatus that facilitates thawing and warming of the frozen tissue and cryopreservation media inside the tissue container, and can also warm the tissue recovery media as well. The regulator apparatus can identify the type of tissue based on an ID tag (e.g., NFC or RFID tag) on the tissue container and automatically apply an appropriate algorithm for thawing, culturing, and maintaining the tissue in a viable state until ready for use (e.g., implantation in a patient, testing, etc.). In some embodiments, the regulator apparatus can control the recovery, culturing, and maintenance processes in a nearly fully-automated manner once the tissue container is inserted in the recovery device and the recovery device is inserted in the regulator apparatus.

The recovery device conducts the tissue recovery media from the at least one recovery media chamber into the tissue container in the tissue container receptacle, and conducts waste media (e.g., including the thawed cryopreservation media) from inside the tissue container into the waste material chamber, while maintaining the tissue container and media in a sterile, contained environment providing controlled temperatures, gas levels (e.g., carbon dioxide levels), and/or parameters.

In some embodiments, the device can comprise a first housing component that includes the at least one recovery media chamber and a second housing component that includes the waste material chamber, such that the first and second housing components are attachable to each other and detachable from each other. The tissue container receptacle can be defined between the first and second housing components when the first and second housing components are attached together. Each component can include engagement means, such as threads or interlocking members, to secure the two components together around the tissue container in a sealed manner. The tissue container can be removable from the tissue container receptacle by detaching the first and second housing components from each other.

The device can further comprise at least a first puncturing element (e.g., a needle) that creates at least a first opening in the received tissue container to permit conduction of recovery media into the tissue container from the recovery media chamber, and at least a second puncturing element (e.g., another needle) that creates at least a second opening in the received tissue container to permit conduction of waste media from the tissue container to the waste material chamber. The puncturing elements can comprise internal conduits that conduct the fluid flow. In some embodiment, the puncturing happens when the container is inserted into the device, or when the two components are secured together. On other embodiments, the puncturing can be automated to occur after the tissue container is sealed inside the device.

The at least one recovery media chamber can comprise two or more recovery media chambers configured to contain two or more different tissue recovery medias. For example, one media can be applied to one side of a sheet of tissue while another media is applied to an opposite side the sheet of tissue.

In some embodiment, the recovery media chamber can receive an insertable and removable media container containing the tissue recovery media. The insertable and removable media container can comprise a manually actuatable mechanism to cause a desired amount of the recovery media to be conducted from the media container to the tissue container. For example, the manually actuatable mechanism can comprise a plunger or screw-drive actuator. In some embodiment, the recovery media chamber can be fully automated and controlled to dispense media at a predetermined rate. The waste material chamber can also be removable from the device to dispose of received waste materials and can replaceable with an empty waste material chamber. This allows for certain components of the device to be disposable, replaceable, and/or sterilizable without having to dispose of or sterilize the entire device between each new use.

The tissue container itself can comprise a container basin, a tissue well positioned inside the container basin, a tissue positioned inside the tissue well, cryopreservation media inside tissue well and container basin, a lid sealed to the container basin that seals the cryopreservation media in the container basin, and an identification tag on the container basin, the lid, or the tissue well, that identifies the tissue. In particular applications, the tissue can comprise a sheet of epithelial tissue (e.g., a monolayer of retinal pigment epithelium on a scaffold) and the cryopreservation media comprises sodium alginate. The entire tissue container can be cryopreserved and stored for long periods (e.g., five years or more) and then thawed, cultures, and maintained ready for use by the disclosed devices. In some embodiments, the whole recovery device with the recovery media and the tissue container enclosed inside can be frozen and stored as a unit.

The foregoing and other objects, features, and advantages of the disclosed technology will become more apparent from the following detailed description, which proceeds with reference to the accompanying figures.

BRIEF DESCRIPTION OF THE DRAWINGS

FIG. 7 illustrates the various isolated components of the recovery device of FIG. 6.

DETAILED DESCRIPTION

Figure 1:
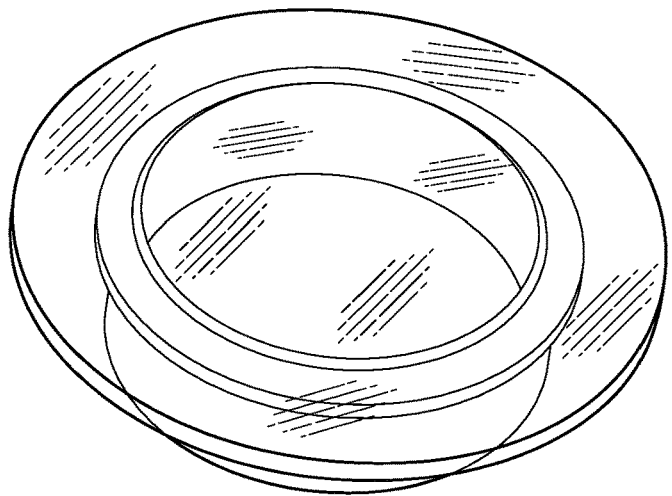
FIG. 1 shows an exemplary tissue well that holds tissue and fluids during cryopreservation and recovery.

FIGS. 1-5 illustrate an exemplary tissue container 22 that contains a tissue or other biological material in a tissue well 12 along with cryopreservation media. The tissue is not shown in the figures. The sealed tissue container 22 can be frozen and stored for long periods of time. Later, the tissue container 22 can be placed in a recovery device, such as the recovery device 30 shown in FIG. 6 or the recovery device 230 shown in FIG. 11, and the frozen tissue can be thawed, cultured, and recovered in a viable state suitable for transplantation into a patient and/or other uses of the tissue. In some embodiments, the tissue can be stored in a cryopreserved state for long periods of time within the recovery device, such as with the entire recovery device being kept in a frozen environment. A regulator apparatus, such as the embodiment 80 shown in FIG. 9 or the embodiment 200 shown in FIG. 11, can be used with the recovery device to carefully monitor and control the thawing, culturing, and recovery process.

Figure 2:
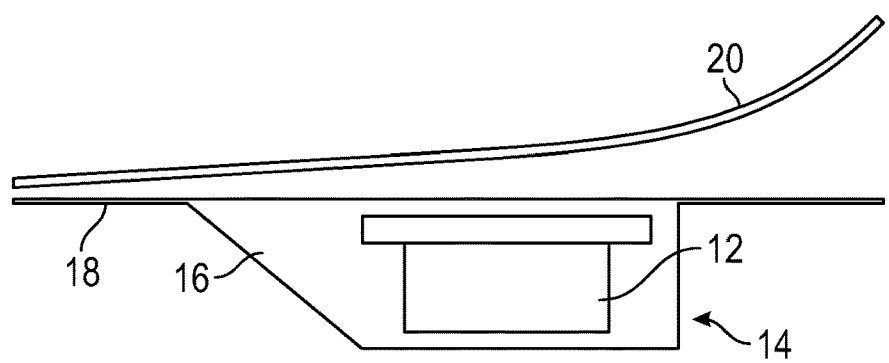
FIG. 2 shows an exemplary sealed container that encloses the tissue well of FIG. 1 with tissue and fluids during cryopreservation and recovery. The container includes a container base and a lid sealed over the top of the base.
Figure 3:
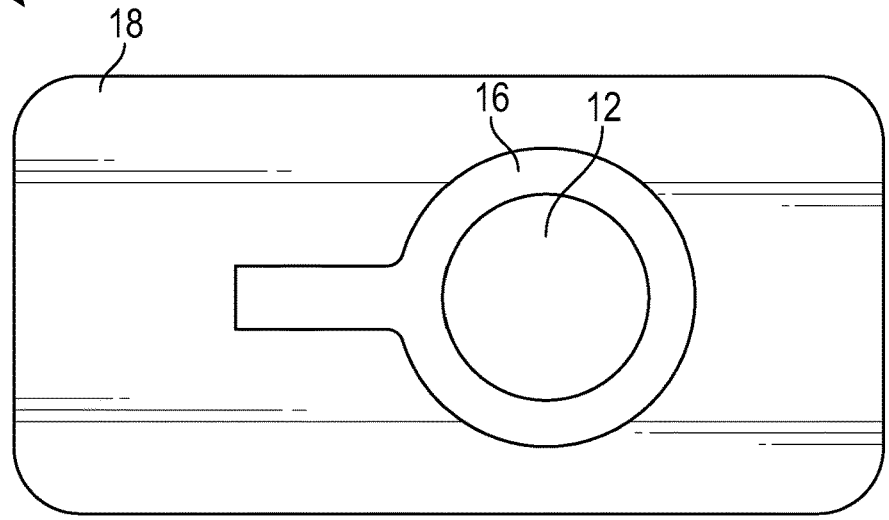
FIG. 3 is a top view of the container base and tissue well of FIG. 2 with the lid removed.
Figure 4:
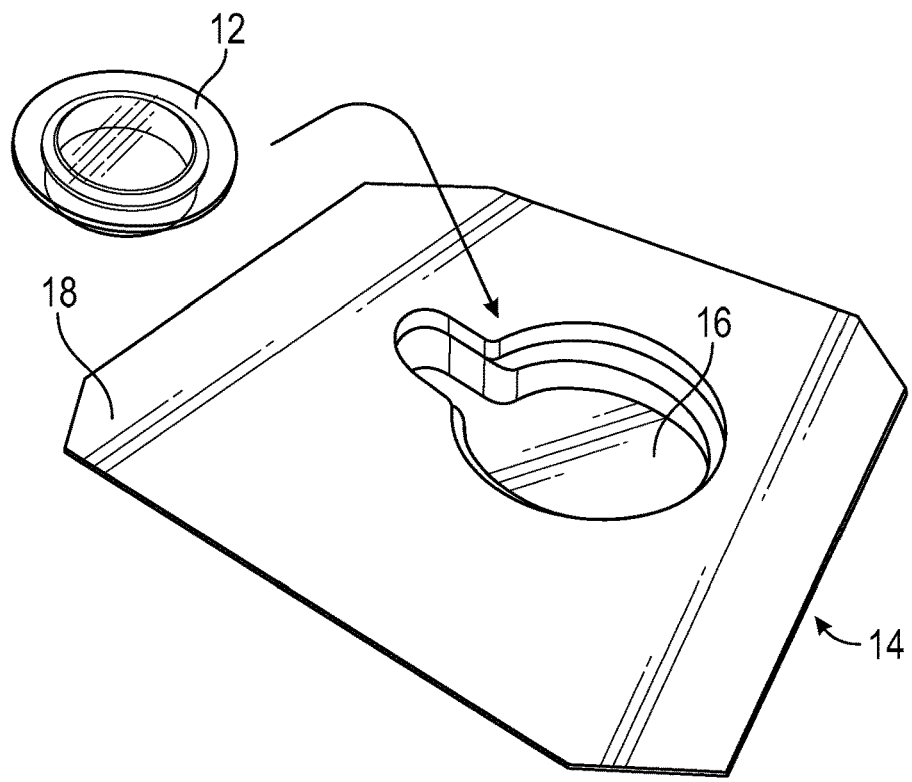
FIG. 4 is a perspective view of the container base and tissue well that goes inside the container base.
Figure 5:
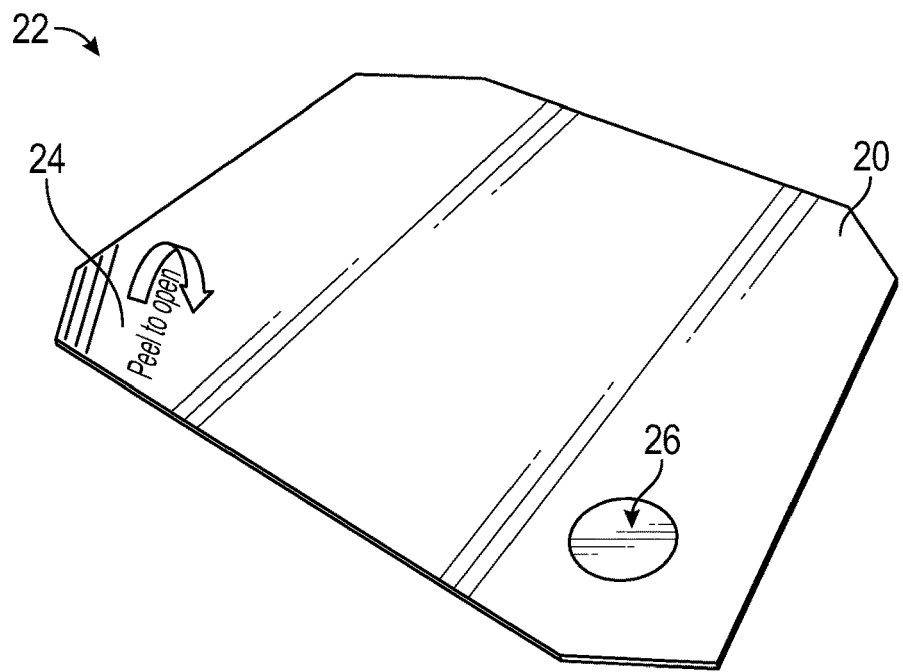
FIG. 5 shows the sealed container with the lid sealed over the container base.

FIG. 1 shows an exemplary tissue well 12 where the tissue is positioned (the tissue itself is not shown, but rests at the bottom of the well 12). FIG. 2 shows the tissue well 12 inside the tissue container 22, which includes a basin 14 and a lid 20 that is sealed over the top of the basin. The basin 14 can include a recessed portion 16 that receives the tissue well 12 (FIG. 4) along with cryopreservation media, and an upper planar surface 18 to which the lid 20 is sealed. As shown in FIG. 5, the lid 20 can include a peelable tab 24 or other feature to facilitate easy removal of the lid 20 when the tissue is ready to be removed. The lid 20, the basin 14, or the well 12 can include an identification tag, such as the tag 26 shown in FIG. 5, that can be read by the recover device, the regulator apparatus, and/or another device, to determine the particulars of the tissue and/or media contained in the tissue container 22. The tag 26 can comprise an NFC tag, an RFID tag, a bar code, a written label, or other suitable identification means. The lid 20 can be sealed to the basin 14 using any suitable means, such as heat sealing.

In some embodiments, the tissue well 12 can comprise a thermoplastic material, such as Splint Material from Keystone Industries, having a thickness of 0.5 to 1.0 mm for example. A sheet of such material can be thermoformed over a mold to form the tissue well. This type of material can provide biocompatibility with the tissue and can survive well during freezing-thawing cycles. Sterilization with ethylene oxide also works well with this type of material.

In some embodiments, a retaining ring can be included inside the well over the tissue sample to hold the tissue in place within the well. The retaining ring can comprise PTFE/Teflon or similar materials, for example. The retaining ring can hold the tissue in place when the well is tilted, turned sideways, turned upside down, etc. The ring can have an opening to allow fluids to flow in and out of the well to interact with the tissue sample.

In some embodiments, the lid 20 can comprise film with an adhesive layer to secure the lid to the basin 14. For example, the lid 20 can comprise polyester label film, such as M-129-461 film or M-114-490 film from BRADY. This type of material is designed to survive liquid nitrogen freezing without losing adhesive properties.

In some embodiments, the tissue container 22 does not include a separate tissue well, like well 12 in FIG. 1, and instead the tissue is placed directly in the basin 14. In other embodiments, other forms of tissue containers or tissue holders can be included inside the tissue container 22 to maintain the tissue is a desired orientation or position. For example, it can be desirable to hold a layer of tissue suspended in media such that both sides of the sheet are exposed to the media, rather than one side resting on a solid surface of the container.

The cryopreserved tissue can comprise any type of biological material, including single-cell suspensions, monolayer tissue sheets, three-dimensional tissue constructs, vascularized tissue constructs, and/or other biological materials. The disclosed technology can be particularly suitable for more complex tissues. One exemplary suitable material comprises a monolayer of retinal pigment epithelium on a scaffold. More information regarding this exemplary tissue material and others, as well as methods for their culturing and transplantation, and other related information, can be found in U.S. Provisional Patent Application No. 62/419,835, filed Nov. 9, 2016, and U.S. Provisional Patent Application No. 62/419,804, filed Nov. 9, 2016, both of which are incorporated by reference herein in their entireties.

The cryopreservation media placed inside the tissue container along with the tissue can comprise any material suitable for the particular tissue and cryopreservation and recovery processes. An exemplary cryopreservation media for use with cryopreserving a monolayer of retinal pigment epithelium on a scaffold can comprise CryoStor® CS2 (commercially available from BioLifeSolutions, Inc., for example) mixed with sodium alginate (e.g., 0.24% sodium alginate). In an exemplary cryopreservation process, such tissue and media, sealed inside a tissue container, can be cooled at a rate of 1° C. per minute.

Figure 6:
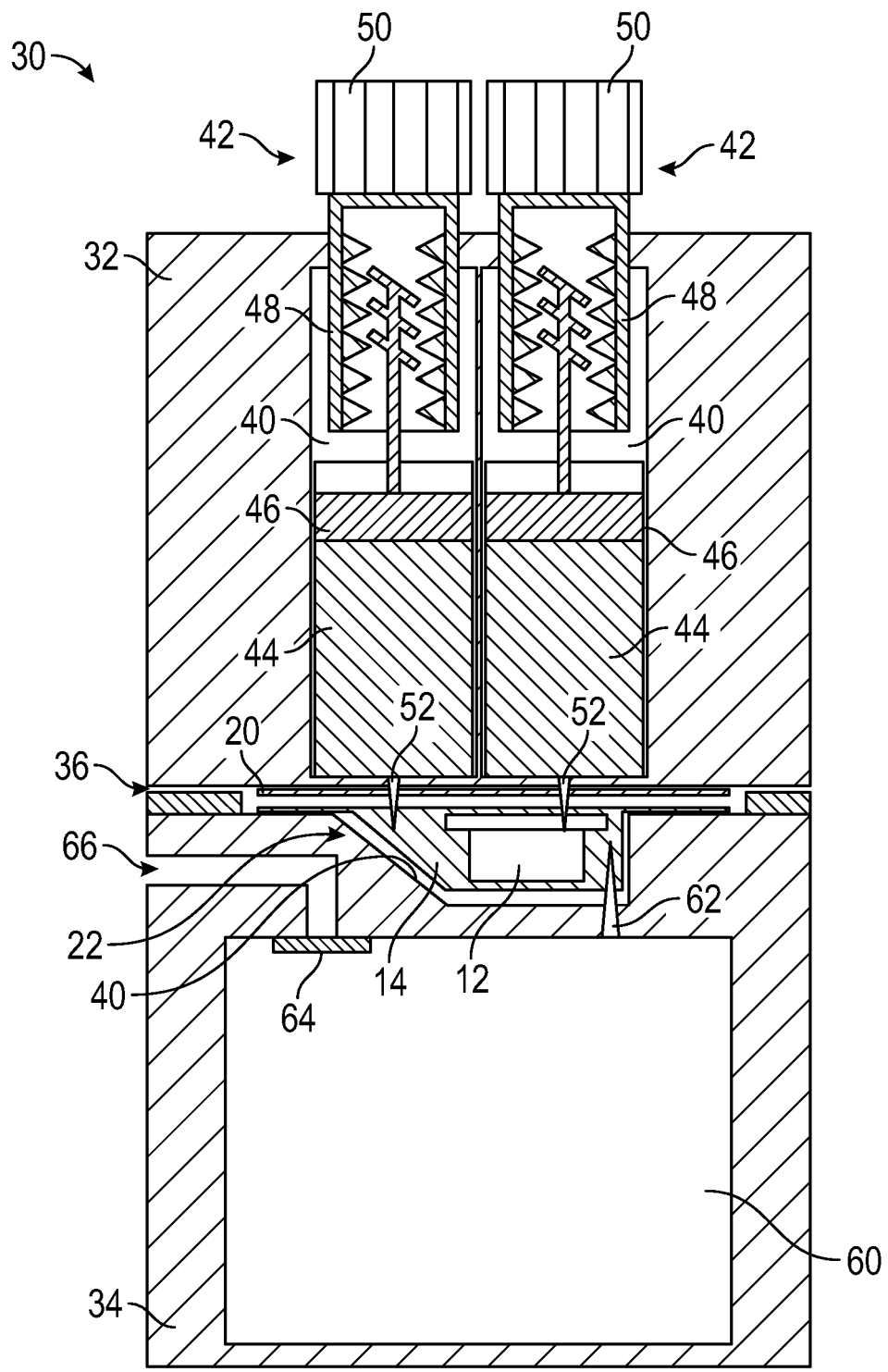
FIG. 6 is a vertical cross-sectional schematic illustrating an exemplary recovery device for recovering frozen tissue that has been stored in a sealed cryopreservation container.

FIGS. 6 and 7 illustrate an exemplary tissue recovery device 30. The device 30 can comprise two main housing components, an upper component 32 and a lower component 34, which can be attached together and detached. In other embodiments, the recovery device does not include two detachable components as illustrated. The device 30 includes a tissue container receptacle, or chamber, 40 configured to receive a sealed tissue container, such as the illustrated container 22. In the illustrated embodiment, the receptacle 40 is defined between the upper component 32 and the lower component 34, such that the tissue container is inserted when the upper and lower components are detached and then the two components are attached together to enclose and/or seal in the tissue container. Engagement and/or sealing features 36 can be included between the upper and lower components to facilitate containment of the tissue container 22. Similarly, engagement and/or sealing features 236 can be included between the upper and lower components 232, 234 of the recovery device 230 (see FIG. 11) to facilitate containment of the tissue container 222. For example, the two components can include mating threaded features, snap-locking features, twist-locking features, magnetic engagement features, and/or other means to attached and detach the two components together. In some embodiments, the device can include an 0-ring or gasket at the interface to help seal in the receive tissue container.

In alternative embodiments, the device 30 can include other tissue container receptacle configurations, such as a slot on the side of the housing with a closable door or lid. In such embodiments, the device 30 need not include two detachable and reattachable housing components.

The tissue recovery device can further comprise at least one recovery media chamber, such as the chamber 40 of device 30, configured to contain a reservoir of tissue recovery media, wherein the at least one recovery media chamber is fluidly coupled to the tissue container receptacle. In the illustrated embodiment, the device 30 includes two chambers 40 that each receive a syringe 42 or similar insertable, removable, and/or replaceable recovery media container. The syringe 42 or similar device can be preloaded with a recover media 44 that is selected for the particular tissue and/or cryopreservation media inside the tissue container 22. The syringe 42 can further comprise manual dispensing features, such as a knob 50 that is rotated to cause inchworm mechanism 48 to push a plunger 46 down to force the media 44 out of the lower outlet 52 (e.g., a needle) of the syringe.

In some embodiments, only one such syringe or other recovery media container is used, while in other embodiment two, three, or more different recovery media containers can be received at the same time in the device 30. Plural different recovery medias can be dispensed to help recover and culture a given tissue. For example, one type of media can be directed to an apical surface of a sheet of tissue and another type of media can be directed to a basal surface of the sheet of tissue. The two can be media dispensed at the same time, sequentially, or in any desired temporal order or pattern.

An exemplary recovery media comprises ROCK inhibitor Y-27632, a cell-permeable, highly potent and selective inhibitor of Rho-associated, coiled-coil containing protein kinase (commercially available from STEMCELL Technologies, Inc.), present in the media at about 10 uM concentration. Such a recovery media can be used to recover a monolayer of retinal pigment epithelium on a scaffold, frozen with a cryopreservation medial comprising CryoStor CS2 mixed with about 0.24% sodium alginate, for example.

With the device 30, the syringes 42 can be manually actuated by turning the knobs 50 to dispense media. In some embodiments, each turn of the knob 50 is calibrated to dispense a predetermined or calculated amount of media. In other embodiments, an automated mechanism can be included to actuate the syringes or other media containers to automatically dispense a selected amount of the media.

The syringes 42 can be removed (e.g., when they are empty or when a different media is desired) and replaced with a new syringe with more of the same media or a different media, as needed. Removed syringes can be disposable and discarded after use, or can be sterilizable and re-filled for re-use. This allows for quick and safe loaded and re-loading of the recovery media syringes while maintaining the rest of the device 30 in use.

When a syringe 42 is inserted, the needle 52 can pass through a hole or sheet of material 70 at the bottom of the chamber 40 of the device 30 and then puncture the lid 20 of the tissue container 22. The dispensed recovery media can then be dispensed into the tissue container inside the device 30 is a sterile manner.

In some embodiments, the outlet needle 52 can comprise a sterile sheath that is mounted around the needle. The sheath can comprise a flexible polymeric material, such as rubber or like. The sheath can initially form a sealed, sterile shield fully surrounding the needle. When the needle is pressed against the lid 20 of the tissue container, the sheath is pinned between the tip of the needle and the lid. The needle then punctures through the sheath and through the lid at the same time, such that the needle and the contents below the lid are maintained in a sterile environment. The sheath sealing against the lid can also help avoid leakage of the liquids out of the puncture made in the lid. Later, then the needle is retracted from the lid, the needle pulls back into the sheath and the sheath can resiliently reseal around the needle, with the rubbery material of the sheath naturally closing the puncture made by the needle, to continue to maintain a sterile environment around the needle, facilitating reuse of the needle and the whole syringe. The needles and sheaths can optionally also be replaceable to ensure sterility. The sheath can allow a regulator apparatus to be reused with multiple recovery devices. Exemplary sheaths suitable for this application include Terumo luer adapters, such as the VENOJECT multi-sample luer adapter (e.g., Terumo XX*MN2000T).

The device 30 can also comprise a waste material chamber 60 fluidly coupled to the tissue container receptacle and configured to receive waste material exiting the tissue container. The waste material can comprise thawed cryopreservation media, the recovery media, and/or other materials from the tissue container. The waste material chamber 60 can also be removable, disposable, and/or replaceable. The waste material chamber 60 can include a pressure relief conduit 66 and/or a filter 64 to allow air to escape but maintain sterility inside the chamber.

The lower component 34 of the device 30 can further include a puncturing element, such as a hollow needle 62, that pierces the basin 14 of the tissue container and allows egress of waste materials from the tissue container toward the waste material chamber 60. The needle 62 can piece the basin 14 as the two components 32, 34 are secured together, or when the tissue container is placed in the receptacle 40 prior to attaching the two components together, or after the two components are attached together. The height of the needle 62 can determined the level of media that remains in the container 22. Media above the level of an opening at the end of the needle 62 drains through the needle into the waste material chamber 60 via gravity. The height of the needle 62 can be selected to leave a sufficient amount of media in the basin 14 at any time, such as enough media to keep the tissue submerged in the media at all times.

Figure 8:
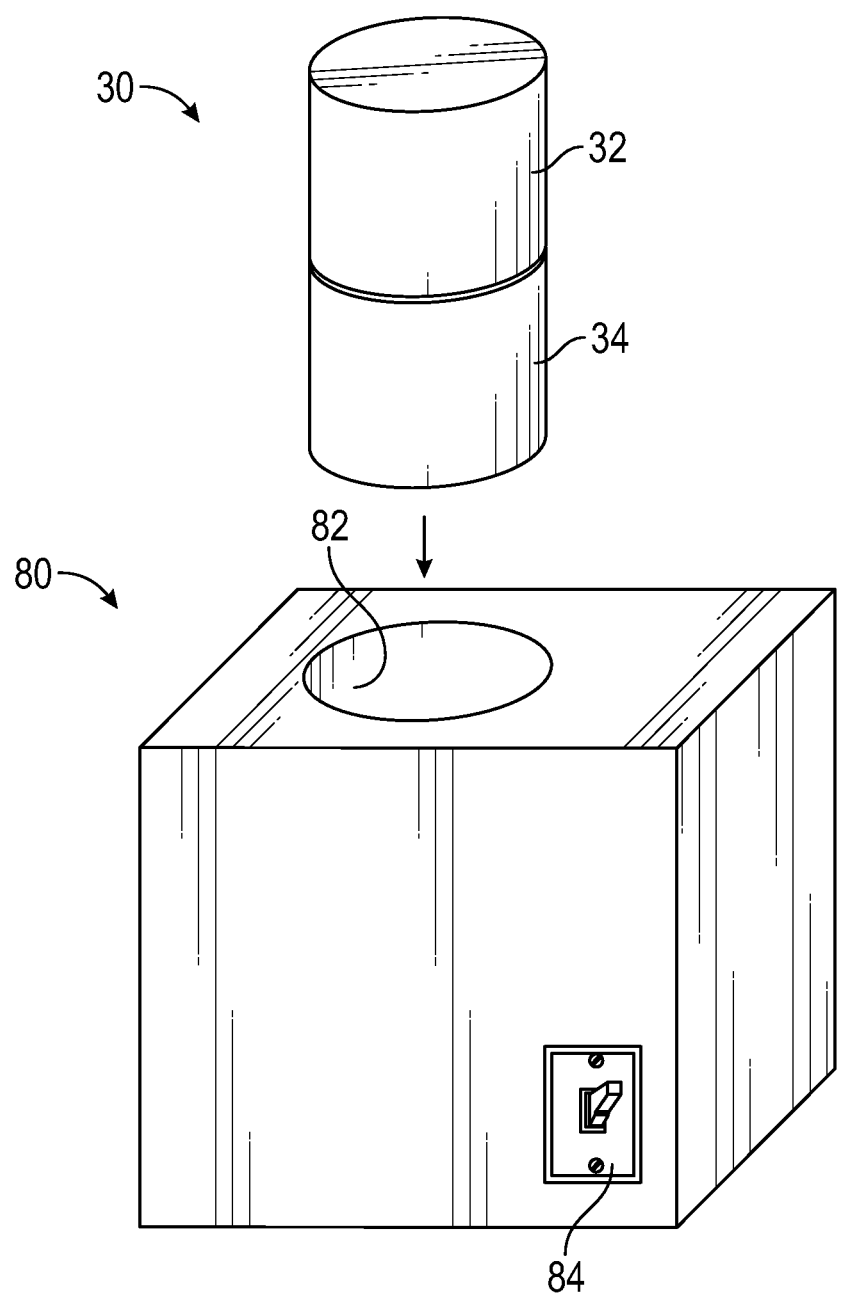
FIG. 8 shows the recovery device of FIG. 6 being inserted into a regulator device that heats the recovery device and regulates the flow of recovery fluids inside the recovery device.

As shown in FIG. 8, after the frozen tissue container is loaded into the recovery device 30, the device 30 can be loaded into a regulator apparatus 80. The regulator 80 can detect the contents of the tissue container and/or the recovery media, can provide heating to thaw and warm the materials inside the device 30 using heaters, and can monitor, manage, and maintain the tissue recovery process using sensors, software and computing components.

Figure 9:
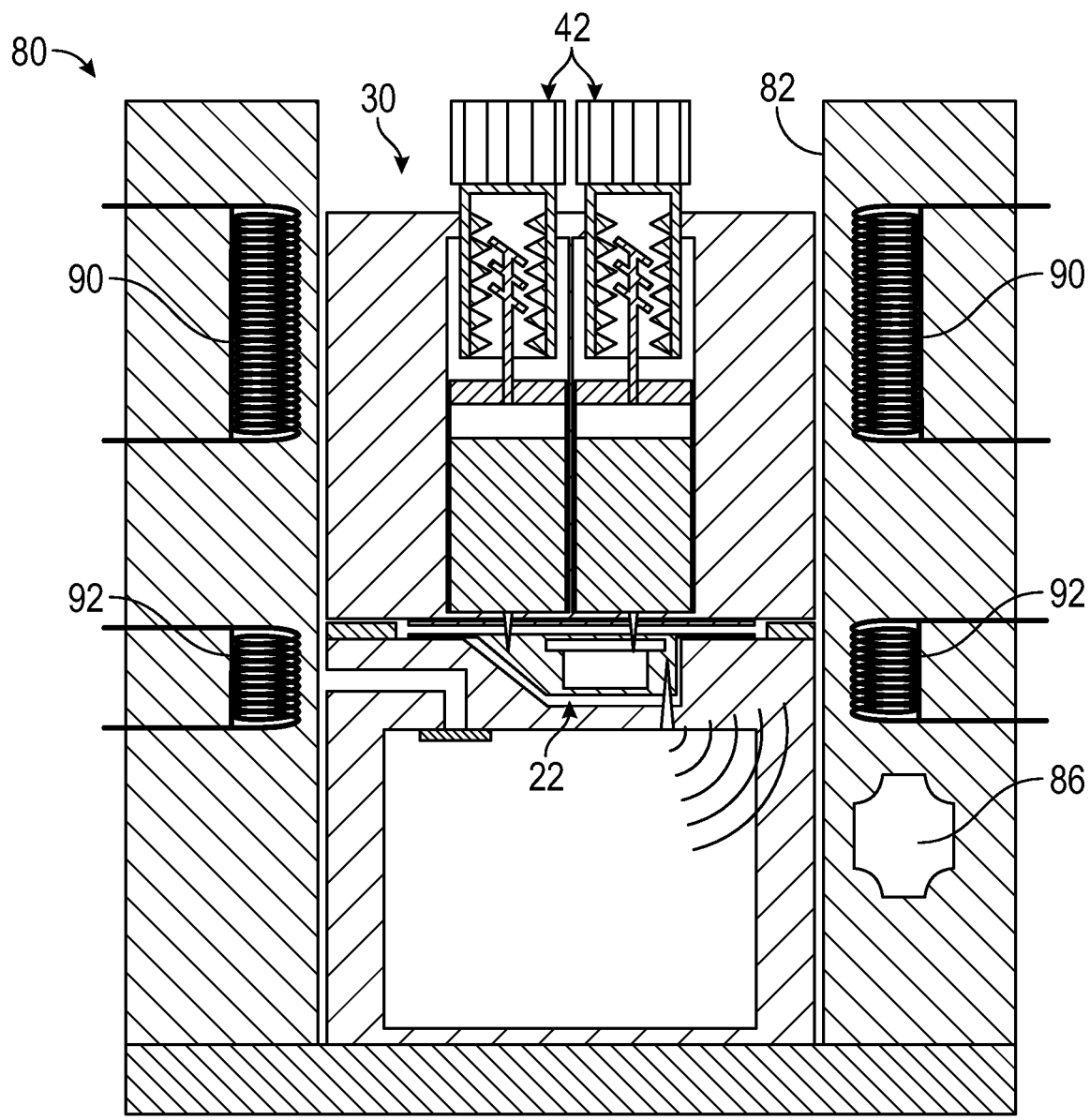
FIG. 9 is a vertical cross-sectional schematic illustrating the recovery device of FIG. 6 placed in the regulator device of FIG. 8, with the regulator device detecting the properties of the recovery device via an NFC tag reader.

FIG. 9 is a cross-sectional view of an exemplary regulator apparatus 80 with a recovery device 30 inserted in a recess 82 of the apparatus. The device 30 contains a frozen tissue container 22 and is loaded with recovery media syringes 42. A sensor 86 (e.g., an NFC, RFID, or barcode reader) in the apparatus 80 can read a corresponding ID tag (e.g., tag 26 in FIG. 5) on the tissue container 22 to determine information about the tissue and/or the cryopreservation media in the tissue container 22. The apparatus 80 can be powered by an electrical cord plugged into a wall outlet or via any other power means. The apparatus 80 can further include an on/off switch 84 (FIG. 8), an automatic power-on mechanism that is triggered by the sensed insertion of the device 30, and/or various other control features. The apparatus 80 can include various computing and control components such as a processor, memory, sensors, user input devices, output devices such a display and status indicators, firmware, software, etc. For example, the apparatus 80 can be pre-programmed with a specific algorithm for each different type of tissue that might be used with it. Algorithms can further be specific to the type of cryopreservation media, the type of recover media, the type of tissue container, the type of recover device, and/or other variable parameters.

In alternative embodiments, the recovery device and regulator apparatus can be operated manually without electricity. Heating and/or cooling can be performed using chemical means, for example. Recovery media can be manually dispensed in a desired manner by turning knobs or pushing plungers on syringes, for example. For example, the knobs 50 can be rotatable and configured to click at rotation increments to provide feedback to the used as to how much media is dispensed. The device 30 can be configured so that a desired amount of recovery media is dispensed with each click of the knob 50, for example.

Once the contents of the device 30 and/or tissue container 22 are identified, the apparatus 80 can apply heat to the recovery media in the syringes 42 using heaters 90 and can apply heat to the tissue container 22 using heaters 92. The recovery media 44 in the syringes 42 may be initially frozen when inserted into the device 30, and therefore may need to be thawed and warmed to a functional temperature before introduction into the tissue container. The apparatus can be pre-programmed to adjust heating levels and heating sequences to optimize the process for the specific frozen tissue detected by the sensor 86. The apparatus 80 and/or device 30 can include temperature sensors to monitor the temperatures of the recovery media and/or the tissue container. The recovery media can be warmed to a desired temperature and maintained ready for introduction into the tissue container 22 before the tissue container is thawed, to minimize the duration when the tissue is thawed prior to transplantation into a patient or other use, and prolong the period of time when the tissue is fully recovered and maintained in a state ready for use. The apparatus 80 can include visual and/or audio indicators that let a user know the current status of the tissue, its remaining viable lifespan, and/or other useful information.

Once the cryopreservation media in the tissue container 22 is thawed and warmed sufficiently, the recovery media 44 can begin to be conducted from the syringe 42 or other recovery media container into the tissue container. As recovery media enters the tissue container, the thawed cryopreservation media is expelled or flushed out of the tissue container into the waste material chamber 60. The recovery media can continue to be introduced into the tissue container at desired rates and in desired sequences to recover the tissue from cryopreservation, flush out undesirable cryopreservation media, and culture the tissue inside the device 30, allowing the tissue to be brought to a viable state inside the sterile confines of the container 22 and device 30, and maintained in the viable state for a prolonged time period, such as several days or weeks, such that the tissue can be kept ready for immediate use at the location (e.g., operating room) where the tissue may be used. In some embodiments, a user can turn the knob 50 of the syringe 42 (or perform similar actions) once every day or once every two days to dispense fresh recovery media and maintain the tissue in a viable state.

When the recovered tissue is ready for use, the device 30 can be removed from the apparatus 80, the top and bottom components 32 and 34 can be detached and the tissue container 22 removed from the device 30. The lid 20 can then be peeled off and the tissue removed from the well 12 in the basin 14. Opening the lid 20 can be accomplished without compromising the sterility of the biological material in the tissue container 22. Further steps may be taken to prepare the tissue for its particular intended use, such as transplantation into a patient. The empty tissue container can then be thrown away. After the tissue container is removed, the device 30 can be prepared for its next use by removing the syringes 42 and the waste material chamber 60. New syringes filled with fresh recovery media can be inserted into the device 30 and a new empty waste material chamber 60 can be inserted into the device. The device 30 is then ready to receive a new frozen tissue container and start the recovery and culturing process over again. In some embodiment, the housing of the device 30 need not be sterilized between uses, minimizing set up time.

Figure 10:
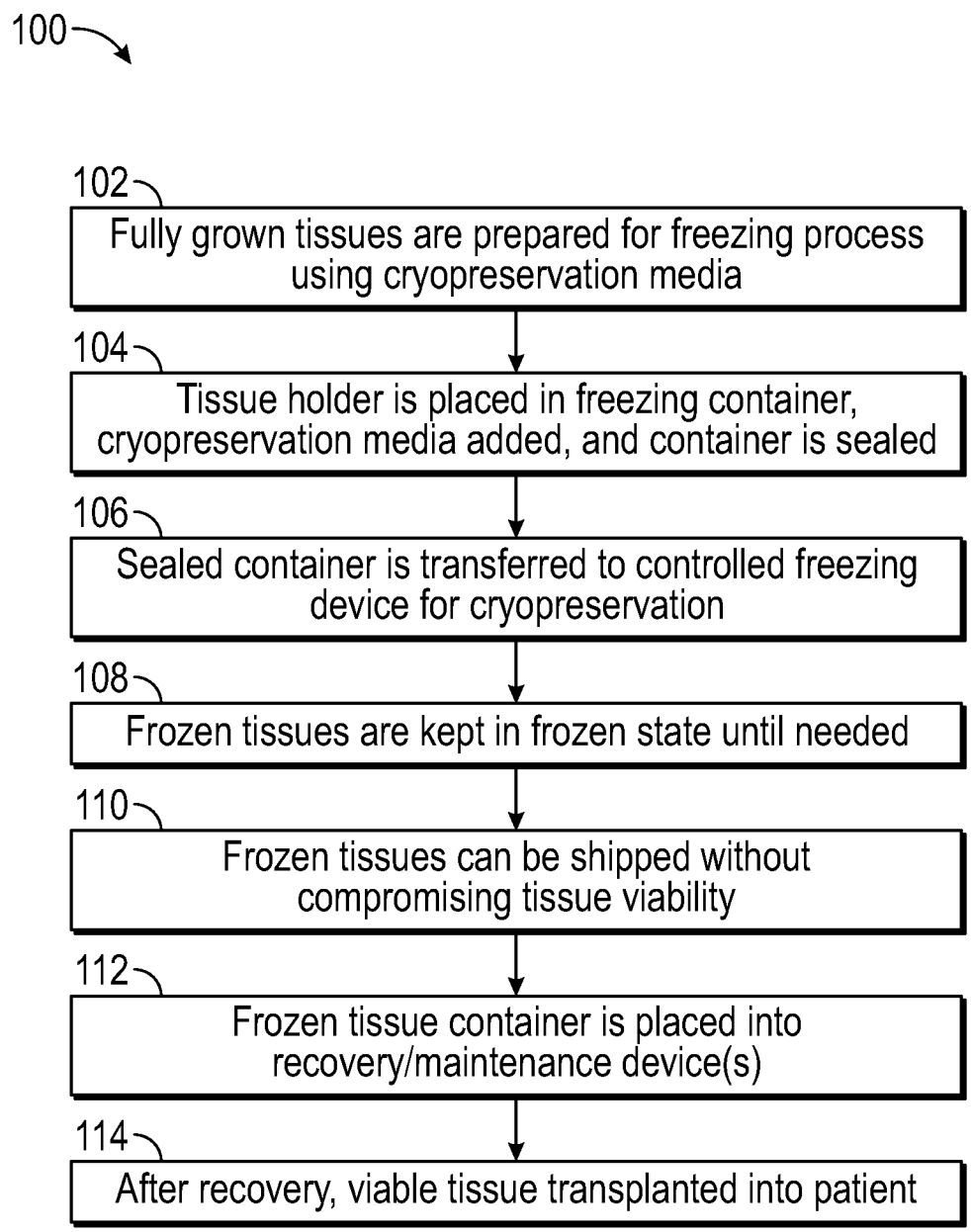
FIG. 10 is a flow chart illustrating an exemplary method for cryopreservation, storage, transport, and recovery of tissue.

FIG. 10 is a flow chart illustrating an exemplary method 100 for cryopreservation and recovery of tissue using the disclosed technology. At 102, fully grown viable tissue is prepared for the freezing process using a cryopreservation media. At 104, a well holding the tissue is placed in the tissue container, cryopreservation media is added, and the tissue container is sealed. At 106, the sealed tissue container is placed in a controlled freezing device for cryopreservation. At 108, the tissue can be kept in the frozen state inside the tissue container for prolonged periods of time, such as several years, until needed. At 110, the frozen tissue container can be shipped or transported as needed while still frozen without compromising the viability of the tissue. At 112, the frozen tissue container is placed into the recover device when it is desired to recover the tissue back to a viable state, and the recovery device is then inserted into the regulator apparatus to control the recovery and culture process and maintain the tissue in the viable state. At 114, the viable recovered tissue can be removed from the tissue container and transplanted into a patient.

Figure 11:
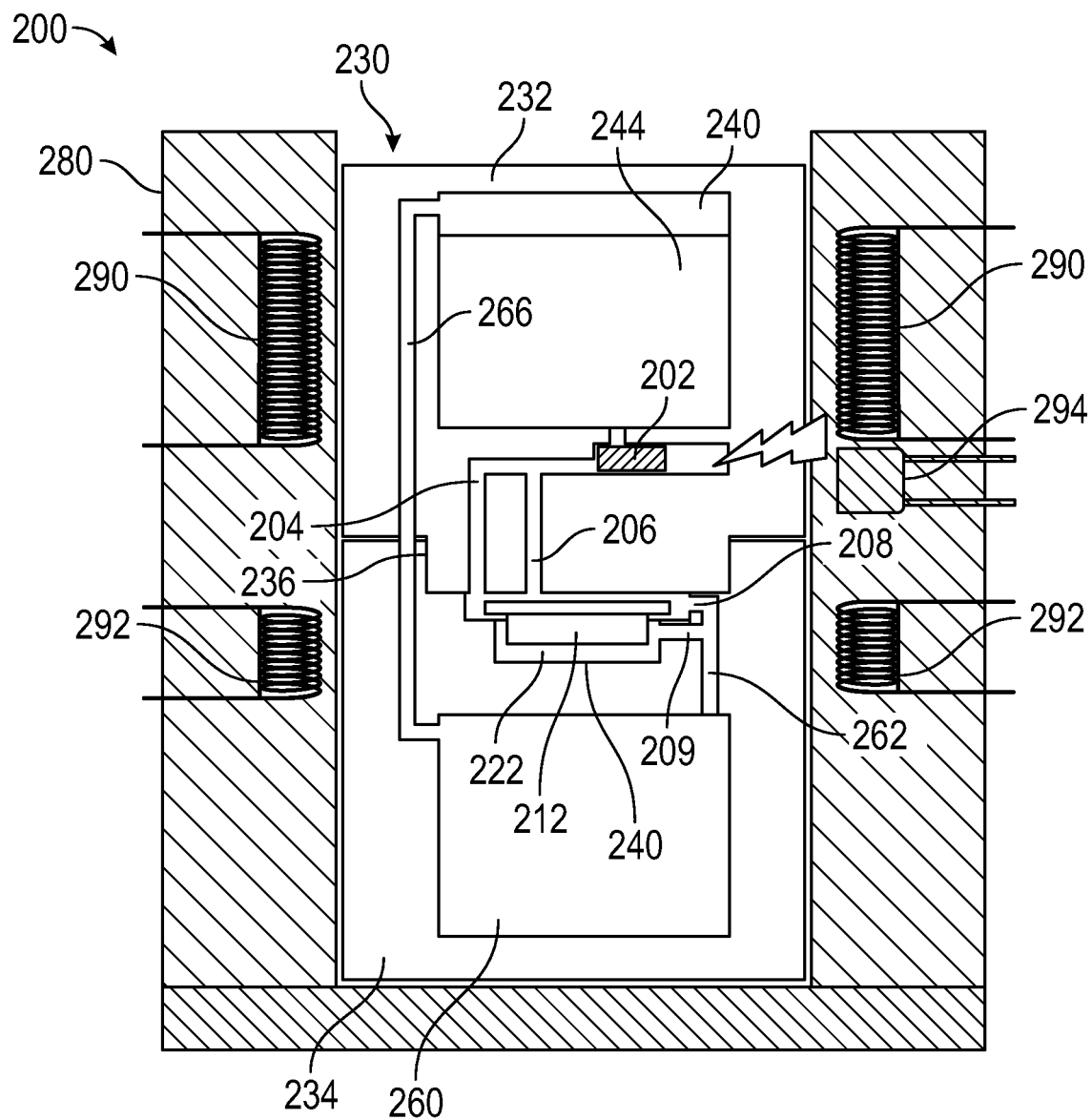
FIG. 11 is a vertical cross-sectional schematic illustrating another exemplary recovery device inside another exemplary regulator device.

FIG. 11 illustrates another exemplary regulator apparatus 200 and corresponding recovery device 230. The regulator apparatus 200 and recovery device 230 have the same general functions as the regulator apparatus 80 and recovery device 30, but with some differences. The regulator apparatus 200 can comprise an outer structure 280 that receives the recovery device 230. The device 230 includes an upper housing component 232 and lower housing component 234 that detach to allow insertion of a tissue container 222 into a receptacle between the two components. The top component 232 includes a recovery media chamber 240 containing recovery media 244, and the lower component 234 includes a waste material chamber 260.

In this embodiment, there are not removable and replaceable syringes containing the recovery media, but instead the chamber 240 in the top component 232 can be refilled with recovery media as needed, such as via a sealable port in the top component. Similarly, the waste material can be emptied from the chamber 260 via a port in the lower component. Alternatively, the chambers 240 and 260 can comprise removable enclosures that are insertable and removable from the device 230, so that can be disposable and/or sterilizable.

The device 230 further comprises a valve 202 that determines when recovery media is allowed to flow from the chamber 240 to the tissue container 222. The valve 202 can be controlled by a valve controller 294 in the apparatus 200 (illustrated in FIG. 11). In one example, the valve controller 294 can comprise a magnetic device that actuates the valve using magnetic fields. Using the valve controller 294, the main control system of the apparatus 200 can determine when to release recovery media and how much to release, and in what sequences.

The device 230 can optionally include more than one recovery media chamber 240 holding different types of recover media.

Figure 12:
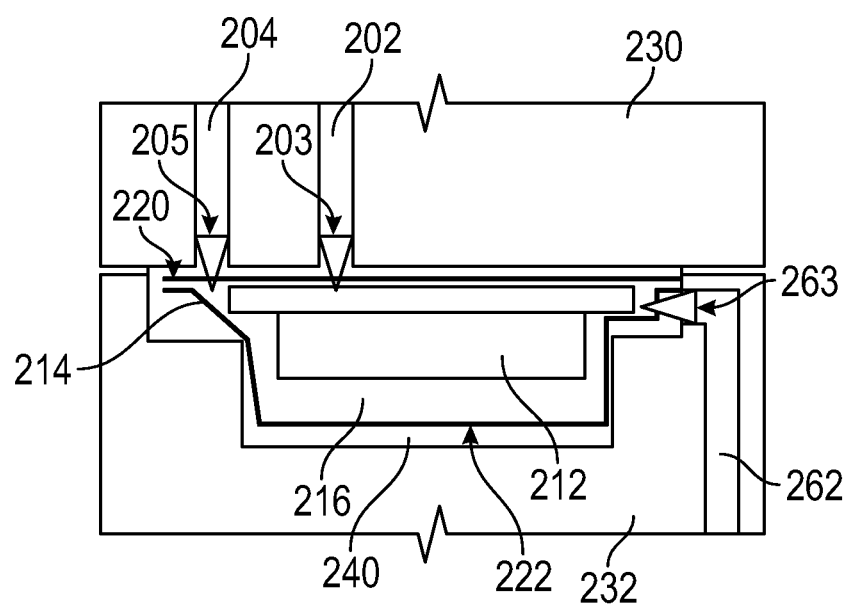
FIG. 12 is an enlarged view of a tissue-containing container mounted inside the recovery device of FIG. 11 and being punctured by needles of the recovery device to allow recovery fluid to flow through the container.

The device 230 can also optionally include more than one conduit to direct recovery media to different portions of the tissue container. For example, as shown in FIG. 11 and FIG. 12, a first conduit 204 can direct media via a first needle 205 through the lid 220 of the tissue container 222 such that the media fills the basin 214 below the tissue holder 212. A second conduit 202 can direct media via a second needle 203 through the lid 220 into the tissue holder 212. In other embodiments, the one conduit can conduct a first media to an apical side of the tissue and a second conduit can conduct a second different media to a basal side of the tissue.

An exit conduit 262 conducts waste media from the tissue container 222 down to the waste material chamber 260. FIG. 12 shows an embodiment with a single exit conduit 260 having a single needle 263 that punctures the side of the tissue container at a desired level. In some embodiments, as shown in FIG. 11, the exit conduit 262 comprises two exit conduits 208 and 209. The upper exit conduit 208 can drain waste material that overflows from the tissue holder 212 for from an apical surface of the tissue, while the lower exit conduit 209 can drain waste material from the basin 214 or from the basal side of the tissue. Each exit conduit can have its own needle and puncture a separate hole in the tissue container.

Figure 13:
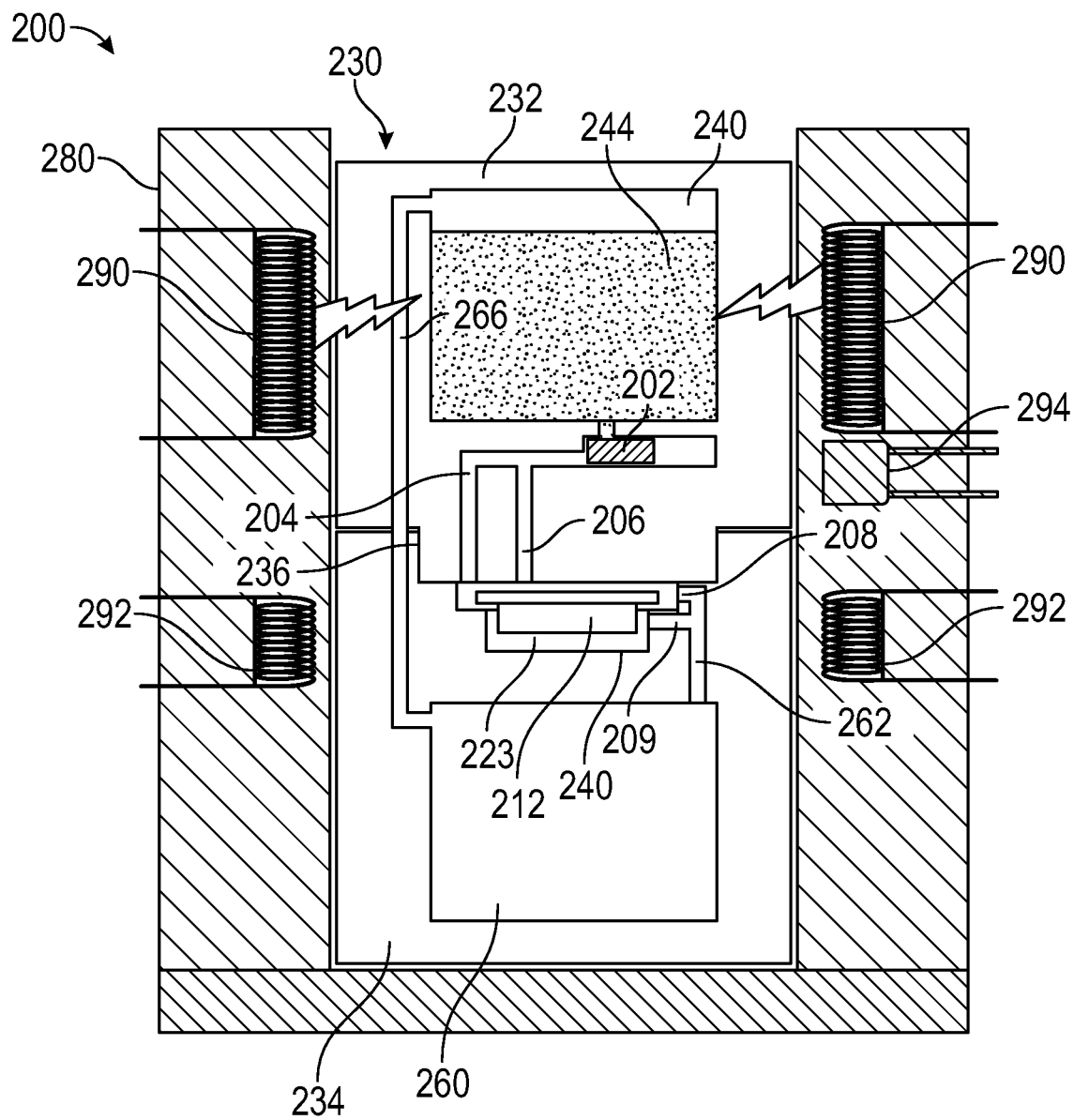
FIG. 13 shows heaters of the regulator device of FIG. 12 warming recovery fluid in a top portion of the recovery device.
Figure 14:
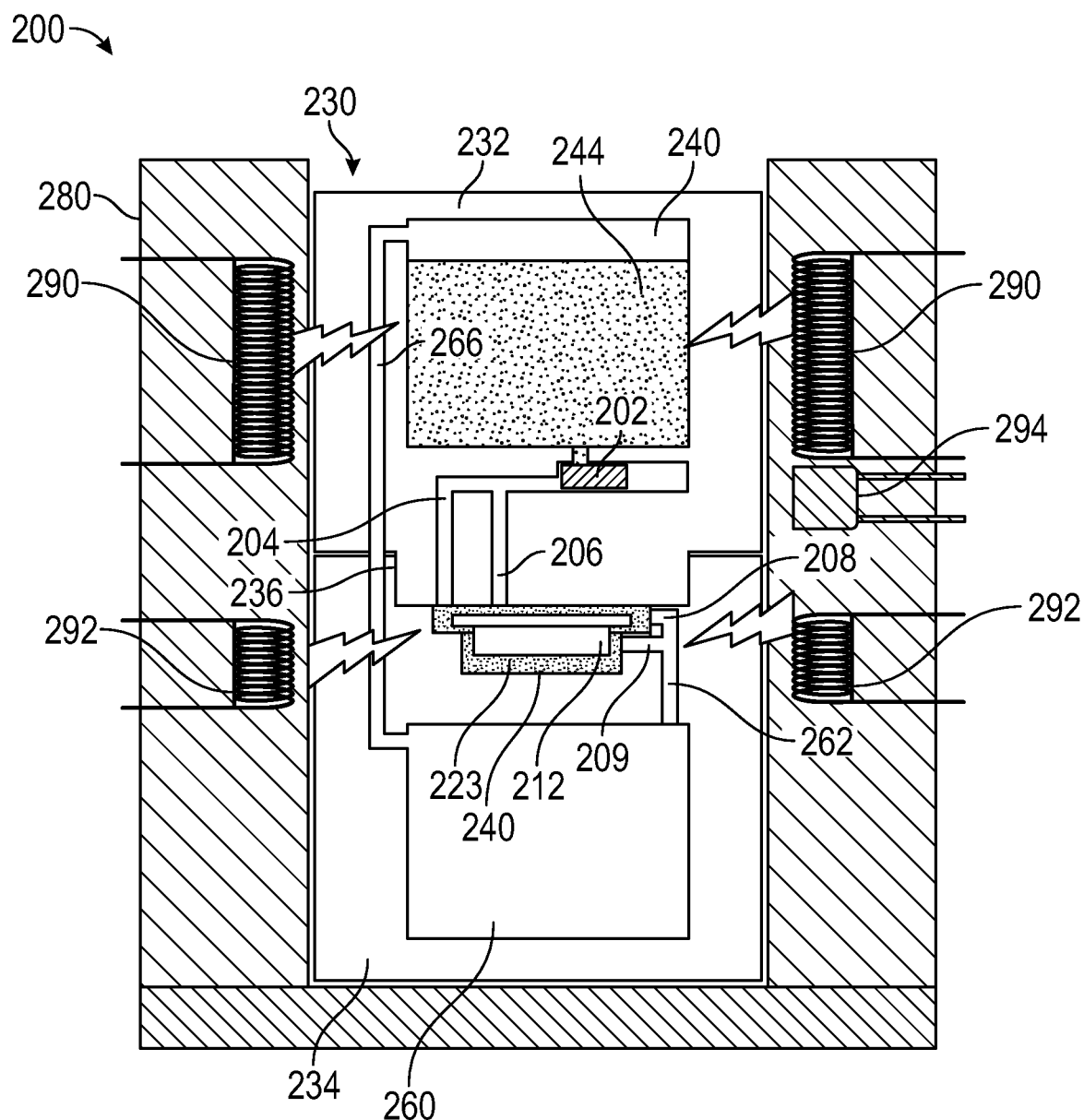
FIG. 14 shows heaters of the regulator device of FIG. 12 warming the recovery fluid in a top portion of the recovery device and warming the frozen contents of the tissue container.
Figure 15:
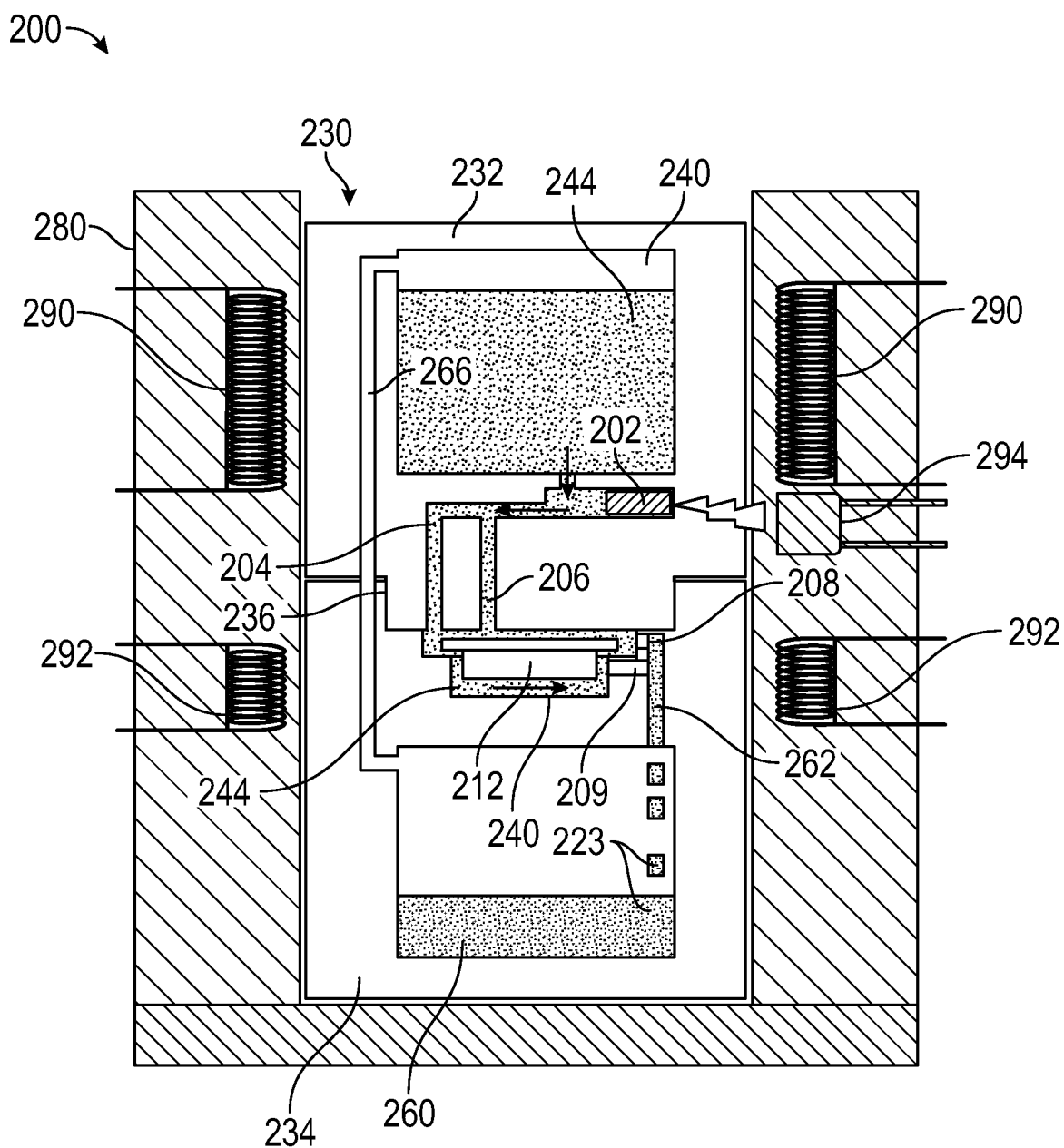
FIG. 15 shows the regulator device of FIG. 12 causing a valve inside the recover device to actuate to allow recovery fluid to flow into the tissue container and push waste fluids into a lower waste container of the recovery device.
Figure 16:
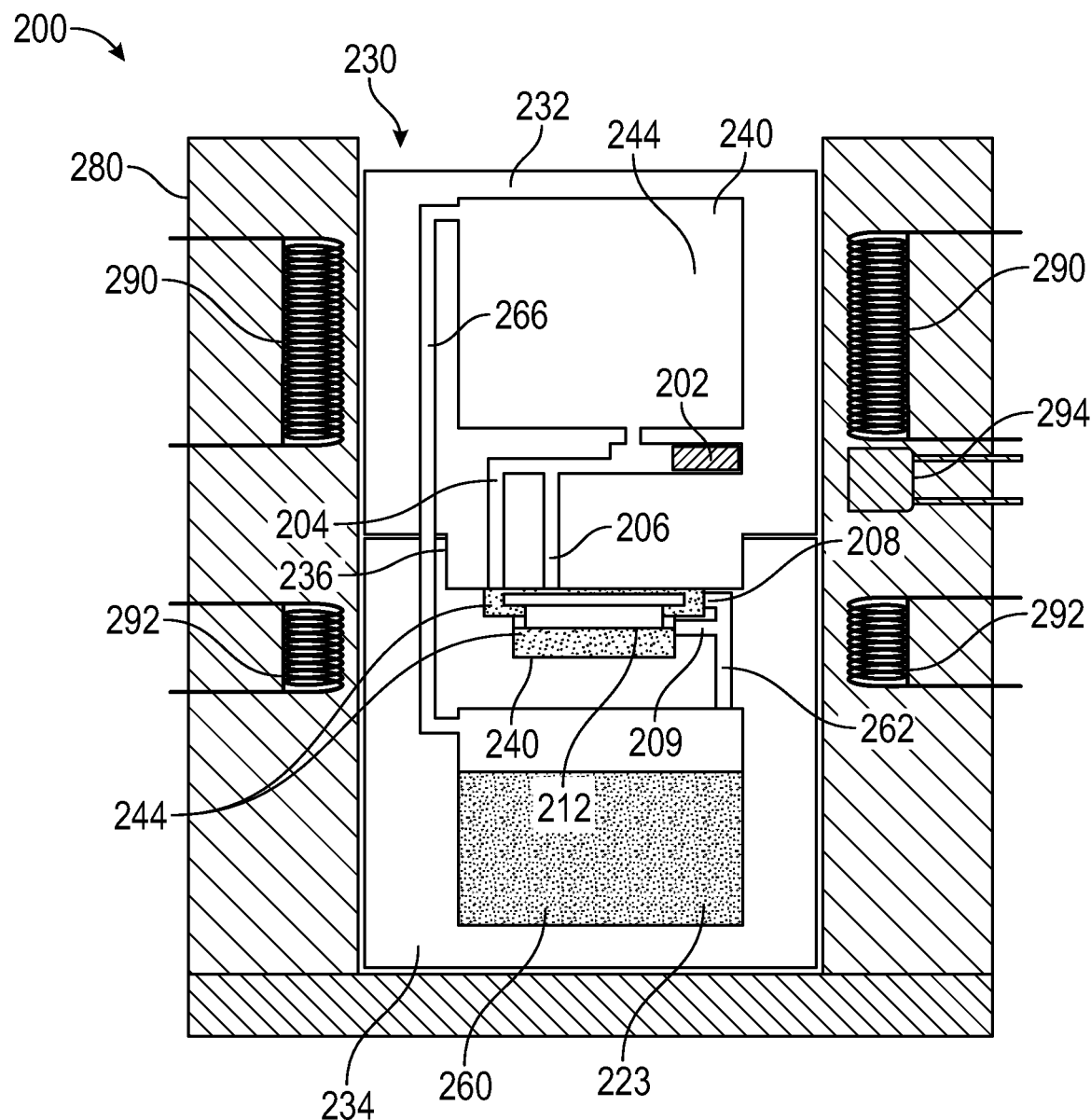
FIG. 16 shows the status of the recovery device of FIG. 12 after the recovery fluid has passed through the tissue container and flushed the fluid contents of the tissue container into the lower waste container, leaving some recovery fluid left in the tissue container.

FIG. 13 illustrates heaters 290 of the apparatus 200 initially heating the recovery media 244, e.g., from a frozen state, while the valve 202 remains closed and the tissue container 222 and the cryopreservation media 223 inside is still frozen. FIG. 14 illustrates heaters 290 of the apparatus 200 continuing to provide heat to the recovery media 244, e.g., to maintain it at a desired temperature, while the valve 202 remains closed and the tissue container 222 and the cryopreservation media 223 inside are being thawed and warmed by heaters 292 in the apparatus. When the tissue container 222 and its contents are sufficiently warmed up, FIG. 15 illustrates the valve 202 being opened by the valve controller 294 to allow the recovery media 244 to flow into the tissue container 222 and flush the cryopreservation media 223 to flow out into the waste material chamber 260. This flow process can continue in stages or sequences as needed to flush out the toxic cryopreservation media 223, replace it with the recovery media 244, and culture the tissue to a viable state while the heaters 292 maintain the tissue container at a desired temperature. A pressure relief conduit 266 can couple the chambers 240 and 260 to maintain pressure equilibrium between the two. FIG. 16 shows the device 230 after all the recovery media 244 has flowed out of the chamber 240 and the flushed cryopreservation media into the waste material chamber 260, along with most of the recovery media that has passed through the tissue container. Some of the recovery media 244 remains inside the tissue container. At this point, the recovery media chamber can be refilled with more recovery media, or replaced with a full chamber of recovery media, or it can remain in a steady state as shown in FIG. 16, maintaining the tissue in a viable state for a period of time until use.

In some embodiments, the tissue container 222 can be rotated about 90 degrees to a vertical orientation during the flushing and recovery process illustrated in FIGS. 15 and 16. By turning the tissue container 222 vertically, gravity can assist the flushing process by reducing mixing of fresh and old media within the container, accelerating the process of media replacement, and require less recovery media. In the horizontal position illustrated, the recovery media flows generally horizontally across the container 222 from in the injection point(s) 203, 205 to the outlet point 263. This horizontal flow results in the replacement of the cryopreservation media by a more gradual, turbulent mixing of the two medias, as gravity acts perpendicular to the primary flow direction. Thus, more recover media is needed to completely flush out the cryopreservation media (e.g., 40-50 ml of recovery media in one example). By contrast, when the tissue container is oriented vertically, a more linear flow occurs in the container as the recovery media enters at the top and pushes the cryopreservation media downwardly in conjunction with gravity toward the lower outlet. This results in less turbulence and a more efficient flushing process, requiring substantially less recovery media (e.g., 5-10 ml of recovery media in one example). To place the tissue container in a vertical orientation, there are a various different optional embodiments. In some embodiments, the entire regulator apparatus 200 can simply be turned 90 degrees (e.g., manually with via an automated system) during the flushing process. In some embodiments, the regulator apparatus 200 can be configured horizontally such that the recovery device 230 is inserted horizontally into an opening at the side instead of the top. In some embodiments, the recovery device 230 can be configured to hold a tissue container 222 in a vertical orientation instead of a horizontal orientation as shown, with the needles puncturing the lid from the side, etc. In some embodiments, the tissue container 222 itself can be configured in a more vertical shape, rather that the short, wide shape illustrated herein. A vertically oriented tissue container 222 can hold the well and tissue sample sideways, for example, relying on the retaining ring in the well to hold the tissue in place within the well.

In some embodiments, collection and/or removal of the waste fluids can be implemented in other manners. In the recovery device 30, a passive waste collection chamber 60 is included to collect waste material from the tissue chamber 22, and the chamber 60 includes a pressure relief conduit 66 to avoid pressure build up in the chamber 60. In the recovery device 230, a pressure relieve conduit 266 is include to relieve pressure build up in the waste collection chamber 260. In other embodiments, active suction can be applied to the waste chamber to reduce pressure in the waste chamber and/or draw waste material out of the waste chamber. In such embodiments, a vacuum pump can be coupled to an outlet of the waste chamber. The vacuum pump can be a separate external device, or can be an integral component of the recovery device or of the regulator apparatus in which the recovery device is placed during defrosting/recovery. In some embodiments, the regulator device can include a vacuum pump and a needle positioned at the bottom or side of the receptacle that receives the recovery device, such that the needle punctures or enters an opening of the waste chamber in the recovery device. The needle can then serve as a conduit to draw waste material and/or air out of the waste chamber via the vacuum pump. The needle can optionally include a protective/sterile sheath around the needle, like as described above with reference to needle 52, to reduce leakage and/or maintain sterility.

In some embodiments, no waste collection chamber is included in the recovery device, and waste materials are drawn directly from the outlet of the tissue chamber to an external location, such as in the regulator apparatus or otherwise.

In some embodiments, a large supply of recovery media can be coupled to one or two or more recovery devices at the same time or sequentially, to facilitate multiple tissue recovery events that occur over a relative short period of time, such as in a busy hospital or clinic. In some embodiments, a large waste material collection chamber can also be coupled to the waste chambers of one or two or more recovery devices, at the same time or sequentially, to further facilitate multiple tissue recover events that occur over a relative short period of time. Waste material can be actively drawn from the recovery devices into the large waste material collection chamber using an active pump or other suitable means.

In some embodiments, the recovery device and/or regulator can control any one or more additional environmental parameters related to the tissue being recovered, such as temperature, carbon dioxide levels, other gas levels, and/or other factors. With regard to controlling carbon dioxide levels, in a conventional cell culture setup, carbon dioxide levels in the incubator work in combination with carbonate buffer in the media to maintain a constant media pH. The requirement for a stable pH can be maintained when a cryopreserved tissue is in the recovery phase, such as when using the disclosed technology. In order to maintain pH with the disclosed technology, a carbon dioxide-independent recovery media can be used, or a means for controlling carbon dioxide levels within the recovery chamber can be implemented. For example, this can be accomplished by chemical means, or by a controlled injection of carbon dioxide gas into the tissue recovery chamber.

In some situations, the disclosed technology can be used to recover and prepare a cryopreserved tissue for a specific use, wherein the tissue is recovered and cultured and then transplanted as soon as it is ready. Such situations could be very time sensitive, e.g., grafting tissue for a burn victim, and the disclosed technology can help increase the speed, safety, and accuracy of the tissue preparation in such cases.

In some situations, the disclosed technology can be used to recover a cryopreserved tissue and maintain the tissue in a viable state, or near viable state, for a prolonged window of time when the tissue may be needed. This can be considered an "on-demand" application of the disclosed technology. For example, in settings where certain tissues are regularly needed, at least one sample of that tissue can be always kept available for on-demand use. When one tissue sample reaches the end of its on-demand "shelf-life" without needing to be used, it can be discarded or possibly re-frozen, and another sample can be prepared to be ready for uses. In this way, a fresh, viable tissue can always be kept available for on-demand use.

The disclosed technology can also make the tissue recovery and transplantation process available to be performed by fewer people, with fewer resources and less infrastructure, and in less carefully controlled environments. Less human input is needed compared to conventional processes, and less risk of complications are introduced. The technology can be used with low risk anywhere the disclosed devices and apparatus can be used, such as wherever there is a power outlet or even without electricity using manual versions of the technology. The disclosed technology can obviate the need for a human to perform several steps of defrosting, culturing, and incubating the tissue (which typically requires these steps to be done using specialized cell culture hoods in a special cell culture room), and then transport the recovered tissue to the surgery room. With the disclosed technology, the thawing, culturing, and maintenance of the viable tissue can all be performed inside a small, self-contained device in an automated or at least simple to control manner.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, elements, and characteristics described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention(s) is not restricted to the details of any foregoing embodiments. The invention(s) extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically, chemically, electrically, magnetically, or otherwise coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of these claims.

The invention claimed is:

1. A device for receiving a sealed tissue container containing cryopreserved tissue and cryopreservation media and for recovering said cryopreserved tissue, the device comprising:
    a first housing component;
    a second housing component, the second housing component being attachable to and at least partially detachable from the first housing component;
    a tissue container receptacle disposed between the first housing component and the second housing component, the tissue container receptacle being configured to receive said sealed tissue container containing cryopreserved tissue and cryopreservation media when the second housing component is at least partially detached from the first housing component, the sealed tissue container being held between the first and second housing components when attached together;
    at least one recovery media chamber configured to contain a reservoir of tissue recovery media, the at least one recovery media chamber being fluidly coupled to the tissue container receptacle; and
    a waste material outlet fluidly coupled to the tissue container receptacle;
    wherein the device facilitates thawing and culturing of the cryopreserved tissue inside the received tissue container by conducting tissue recovery media from the at least one recovery media chamber into the tissue container in the tissue container receptacle, and by conducting waste material including thawed cryopreservation media from inside the tissue container out through the waste material outlet.

2. The device of claim 1, wherein the first housing component includes the at least one recovery media chamber and the second housing component includes the waste material outlet.

3. The device of claim 2, wherein the received tissue container is sealed in the tissue container receptacle when the first and second housing components are attached together, and the tissue container is removable from the tissue container receptacle by detaching the first and second housing components from each other.

4. The device of claim 1, further comprising at least a first puncturing element that creates at least a first opening in the received tissue container to permit conduction of recovery media into the tissue container from the recovery media chamber, and at least a second puncturing element that creates at least a second opening in the received tissue container to permit conduction of waste media from the tissue container out through the waste material outlet.

5. The device of claim 1, wherein the at least one recovery media chamber comprises two or more recovery media chambers configured to contain two or more different tissue recovery medias.

6. The device of claim 1, wherein the at least one recovery media chamber receives an insertable and removable media container containing the tissue recovery media.

7. The device of claim 6, wherein the insertable and removable media container is manually actuatable to cause a desired amount of the recovery media to be conducted from the media container to the tissue container.

8. The device of claim 1, further comprising a waste material chamber fluidly coupled to the waste material outlet, wherein the waste material chamber is configured to receive and store the waste material within the device.

9. The device of claim 1, further comprising at least a first conduit fluidly coupling the at least one recovery media chamber to the tissue container receptacle.

10. The device of claim 1, wherein the device conducts a first recovery media to a first side of the tissue and conducts a second recovery media to a second side of the tissue.

11. The device of claim 1, wherein the waste material outlet is couplable to an active vacuum apparatus for drawing waste material out of the device.

12. The device of claim 9, further comprising a valve, the valve being positioned along said first conduit coupled between the at least one recovery media chamber and the tissue container receptacle.

13. The device of claim 1, wherein the tissue recovery media comprises ROCK inhibitor Y-27632.

14. A regulator apparatus comprising;
a housing having a compartment operable to receive the tissue recovery device of claim 1;
an identification tag reader that reads an identification tag on the tissue container in the tissue recovery device to enable the regulator apparatus to determine identifying information about the tissue inside the tissue container; and
at least a first heater that warms the tissue container inside the tissue recovery device.

15. The regulator apparatus of claim 14, further comprising at least a second heater that warms the tissue recovery media in the recovery media chamber of the tissue recovery device.

16. The regulator apparatus of claim 14, further comprising a control system programmed to control heating of the tissue container by the first heater based at least in part on the identifying information about the tissue to recover the tissue to a viable state and maintain the tissue in the viable state.

17. The regulator apparatus of claim of claim 14, further comprising a valve controller that controls actuation of a valve in the tissue recovery device to regulate the flow of tissue recovery media into the tissue container.

18. A tissue container usable with the device of claim 1, the tissue container comprising:
a container basin;
a tissue well positioned inside the container basin;
a tissue positioned inside the tissue well;
cryopreservation media inside tissue well and container basin;
a lid sealed to the container basin that seals the cryopreservation media in the container basin; and
an identification tag on the container basin, the lid, or the tissue well, that identifies the tissue.

19. The tissue container of claim 18, wherein the tissue comprises a sheet of epithelial tissue and the cryopreservation media comprises sodium alginate.

* * * * *